(12) United States Patent
Itrich et al.

(10) Patent No.: US 7,232,426 B2
(45) Date of Patent: Jun. 19, 2007

(54) CLIP ASSEMBLY PART FOR USE WITH AN ADAPTER TO THE PROXIMAL END OF A PEG TUBE

(75) Inventors: Martin Itrich, Frankfurt am Main (DE); Barbara Breuer-Thal, Hattersheim (DE)

(73) Assignee: Fresenius Kabi Deutschland GmbH, Bad Homburg V.D.H. (DE)

( * ) Notice: Subject to any disclaimer, the term of this patent is extended or adjusted under 35 U.S.C. 154(b) by 119 days.

(21) Appl. No.: 10/486,427

(22) PCT Filed: Aug. 2, 2002

(86) PCT No.: PCT/EP02/08609

§ 371 (c)(1),
(2), (4) Date: Mar. 4, 2004

(87) PCT Pub. No.: WO03/013644

PCT Pub. Date: Feb. 20, 2003

(65) Prior Publication Data

US 2004/0193115 A1    Sep. 30, 2004

(30) Foreign Application Priority Data

Aug. 11, 2001    (DE) .............................. 101 39 644

(51) Int. Cl.
*A61M 5/32* (2006.01)
(52) U.S. Cl. ...................................................... 604/175
(58) Field of Classification Search ................ 604/175, 604/268, 174, 256, 93.01, 178, 910, 905, 604/264; 128/346, DIG. 16
See application file for complete search history.

(56) References Cited

U.S. PATENT DOCUMENTS

| 4,473,369 A | * | 9/1984 | Lueders et al. ............. 604/244 |
| 4,579,120 A | * | 4/1986 | MacGregor ................. 600/392 |
| 4,733,666 A | * | 3/1988 | Mercer, Jr. .................. 606/151 |
| 5,549,657 A | * | 8/1996 | Stern et al. ................. 604/537 |
| 5,792,112 A | | 8/1998 | Hart et al. |
| 6,231,547 B1 | | 5/2001 | O'Hara |
| 2001/0007067 A1 | | 7/2001 | Kurfess et al. |

* cited by examiner

*Primary Examiner*—Nicholas Lucchesi
*Assistant Examiner*—Christopher D. Koharski
(74) *Attorney, Agent, or Firm*—Hamilton, Brook, Smith & Reynolds, P.C.

(57) ABSTRACT

Clip assembly part (3) for use with an adapter to the proximal end of a PEG tube. The clip assembly part (3) is configured as a loose spacer part for the external retaining part of the adapter and comprises elements (14, 15) for fixing the PEG tube to prevent it from sliding back.

8 Claims, 3 Drawing Sheets

CLIP ASSEMBLY PART FOR USE WITH AN ADAPTER TO THE PROXIMAL END OF A PEG TUBE

RELATED APPLICATIONS

This application is the U.S. National Phase of International Application No. PCT/EP02/08609, filed 02 Aug. 2002, published in German, which application claims priority under 35 U.S.C. § 119 or 365 to Germany Application No. 101 39 644.9, filed 11 Aug. 2001. The entire teachings of the above applications are incorporated herein by reference.

The invention relates to an assembly part for an adapter for the subsequent shortening of a PEG tube that has already been fitted for artificial feeding. Moreover, the invention relates to an adapter for a PEG tube comprising an assembly part of this type.

For enteral feeding, PEG tubes are known by means of which a nutrient solution can be passed into the stomach or the intestine of the patient. To fit a PEG tube, a gastroscope or an endoscope is introduced into the patient's stomach and the stomach is expanded by air insufflation. Subsequently, a canula is pushed into the stomach through the abdominal wall and the stomach wall. According to the conventional thread pull-through procedure, a guide thread is introduced into the stomach through the canula, gripped with a gripping tool or similar device of the gastroscope or endoscope and pulled out again through the oesophagus and the mouth of the patient. By means of this guide thread fitted in this way, the tube is then passed to the stomach interior and from there through the puncture site towards the outside. This surgical procedure is also called percutaneous endoscopically controlled gastrostomy (PEG).

The known PEG tubes have, at their distal end, an internal retaining element by means of which the flexible tube is supported on the inner stomach wall. The flexible tube is dimensioned such that it extends some considerable distance beyond the abdominal wall. At its proximal end, the tube is equipped with a connecting part to be able to connect the conduction system for feeding in of nutrient solution.

In practice, the known PEG tubes have proved advantageous. However, the flexible tube protruding relatively far outside of the abdominal wall is considered to be a disadvantage by active and mobile patients.

To fit the adapter, the flexible tube is fixed with surgical forceps or clamps, for example, above the abdominal wall and shortened to the required length. Subsequently, the adapter is connected to the flexible tube protruding from the abdominal wall, the fixing action of the forceps being released. A clamp part is provided at the adapter for fixing the flexible tube.

U.S. Pat. No. 5,549,657 describes an adapter which permits shorting of the flexible tube of a PEG tube that has already been fitted, without the need to change the tube in the case of a flexible tube that is still intact. The adapter has an external retaining element which is supported on the abdominal wall, with a connector for connecting the conduction system to the tube.

Fitting of adapters for PEG tubes of the type described above is rendered difficult because the clamp is relatively large and unwieldy so that the fitting operation is impeded.

The invention is based on the task of creating an assembly part that is secure to handle and simplifies shortening of a PEG tube already fitted to the required length and fixing of the adapter to-the tube. A further task of the invention consists of providing an adapter with such an assembly part.

This task is achieved according to the invention by means of the characteristic features of claims 1 and/or 12. Advantageous embodiments of the invention are the subject matter of the sub-claims.

When the term PEG tube is used in the following, this is intended to mean both the tube as such and the actual flexible tube.

The assembly part according to the invention is configured as a loose spacer part for the external retaining part of the adapter and is used to fix the PEG tube to the abdominal wall of the patient to prevent it from sliding back. Before the adapter is fitted, the PEG tube is fixed to the assembly part. In this way, the PEG tube is secured to prevent it from sliding back. Subsequently, the PEG tube is shortened and the external retaining part of the adapter is fixed to the tube. Preferably, the assembly part is pushed onto the PEG tube until it rests on the abdominal wall.

The assembly part can be pushed onto the abdominal wall as such or together with the external retaining part of the adapter. Preferably, the assembly part forms one unit with the external retaining part, the assembly part being releasable from the retaining part after the adapter has been fitted. Handling is thus simplified.

In a preferred embodiment, the assembly part consist of two parts, namely a retaining housing enclosing the PEG tube, wherein said housing is placed onto the abdominal wall, and a retaining clip which is used to fix the tube onto or to the retaining housing. Preferably, the retaining housing is equipped with a retaining part with a central bore for passing through the PEG tube and gripping part which is advantageously equipped with gripping recesses.

The retaining part and the gripping part of the retaining housing preferably consist of two halves which are connected by means of a hinge, in particular a film hinge. This has the advantage that the assembly part can be easily removed from the tube after the adapter has been fixed. However, the two-part design of the adapter can also be advantageous during assembly because the tube does not need to be passed through the bore in the retaining part but can simply be inserted laterally into the retaining housing and the retaining housing shut by closing the two halves together.

The retaining housing can also consist of two halves not connected together which are held together by the retaining clip. The retaining housing can also consist of a single part and be equipped with an intentional fracture site for dividing it during dismantling.

The retaining clip and the retaining housing may be configured such that the retaining clip can be either pushed into the retaining housing or onto the retaining housing. Preferably, a guide facility is provided on the retaining housing.

In a particularly preferred embodiment, the retaining clip for fixing the tube in the retaining housing is equipped with a slit into which the PEG tube is pushed laterally. The slit contains a first section with a larger diameter than the tube and a second section which has the same diameter as the tube. When the tube is inside the first section of the slit, the assembly part can be displaced easily on the tube. In the second section of the slit, however, the tube is fixed. In this way, the tube can be fixed and/or released in the retaining housing simply by sliding the retaining clip.

In a further particularly preferred embodiment, two stop positions are provided, the first section of the slit of the retaining clip being in alignment, in the first stop position, with the bore of the retaining housing and the second section of the slit of the retaining clip being in alignment, in the second rest position, with the bore of the retaining housing. This has the advantage that the retaining clip can be displaced between two defined positions in which either the assembly part is displaceable on the PEG tube or the tube is fixed to the assembly part.

In the following, a practical example of the invention is described in further detail with reference to the drawings.

Figure 1:
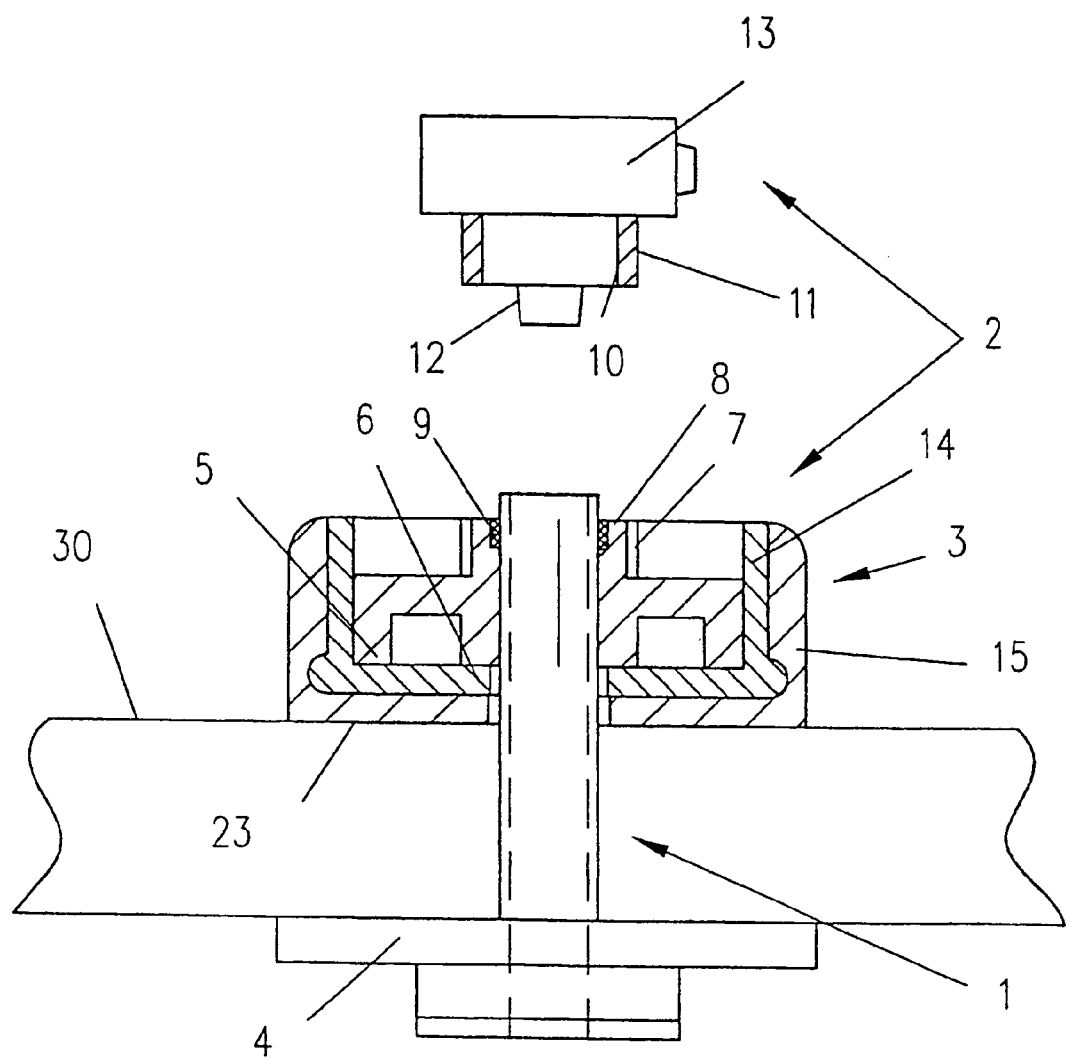
FIG. 1 shows a side view of a PEG tube with adapter and assembly part in a part sectional drawing.

FIG. 1 shows a side view of a PEG tube 1 as a part sectional illustration together with an adapter 2 which is equipped with an assembly part 3. At its distal end, the PEG tube is equipped with a plate-type internal retaining part 4 by means of which the tube is supported on the internal stomach wall. The external retaining part 5 by means of which the tube is supported on the abdominal wall 30 is preferably part of the adapter 2.

The external retaining part 5 of the adapter is a circular disc consisting of a pliable biocompatible material with a central aperture 6 for passing through the tube 1. On its upper side facing away from the patient, the retaining part 5 is equipped with a lower sheath-type clamp part 8 equipped with an external thread 7, into which an elastic clamp ring 9 is inserted through which the tube is passed. In an upper sheath-type clamp part 11 equipped with a corresponding internal thread 10, a conical hollow peg 12 is arranged concentrically onto which the tube is pushed.

To clamp the tube 1 in a fixed position, the lower and upper clamp part 8, 11 are screwed into each other as a result of which the elastic clamp ring 9 exerts a radial clamping force onto the tube.

The top section of the clamp part 11 becomes a positive Luer lock connecting part 13 not illustrated in further detail or a different connector to which the negative Luer lock connecting part of the conduction system, which is not illustrated, for supplying nutrient solution can be connected. In addition, adapter 2 of the tube can, for example, be additionally equipped with a shut-off device or a closure cap integrated into the housing body of the clamp parts.

In the following, the assembly part 3 of the adapter 2 of the PEG tube 1 is described with reference to FIGS. 2 to 5. The assembly part 3 consists of a retaining housing 14 and a retaining clip 15.

Figure 2:
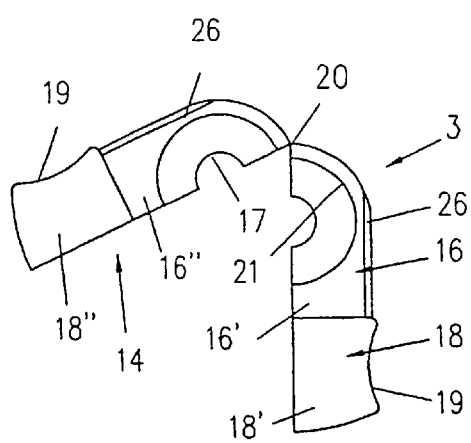
FIG. 2 shows the open retaining housing of the assembly part of the PEG tube of FIG. 1 as a top view.
Figure 6:
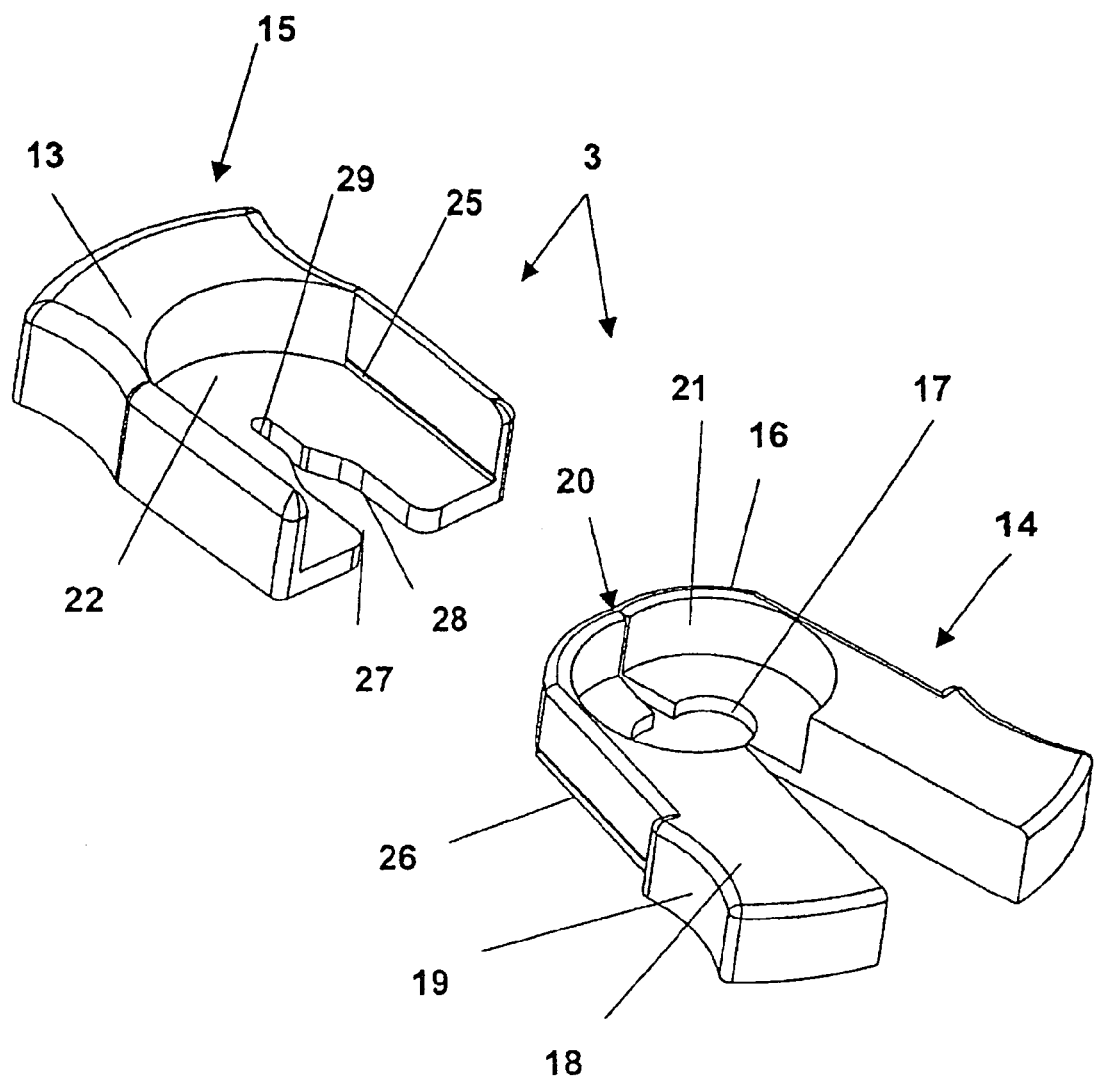
FIG. 6 shows a perspective view of the assembly part.

FIG. 2 shows the open retaining housing 14 as a top view. The retaining housing is equipped with a retaining part 16 with a central bore 17 to which a gripping part 18 with lateral gripping recesses 19 is connected. The retaining part 16 and the gripping part 18 consist of two halves 16', 16" and 18', 18" which are flexibly connected with a film hinge 20 such that the retaining housing can be easily dismantled after the adapter has been fixed to the tube.

A central circular cut-out 21 is provided in the retaining part 16 of the retaining housing 14, the diameter of which is such that the external retaining part 5 of the adapter 2 can be inserted into the cut-out and fixed in it by clamping (FIG. 1).

Figure 5:
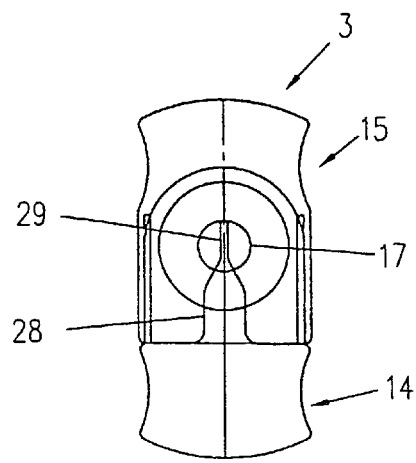
FIG. 5 shows the assembly part of the PEG tube of FIG. 1 as a top view, the retaining clip being in the position fixing the tube
Figure 3:
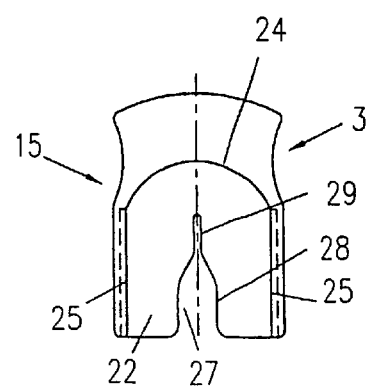
FIG. 3 shows the retaining clip of the assembly part of the PEG tube of FIG. 1 as a top view.
Figure 4:
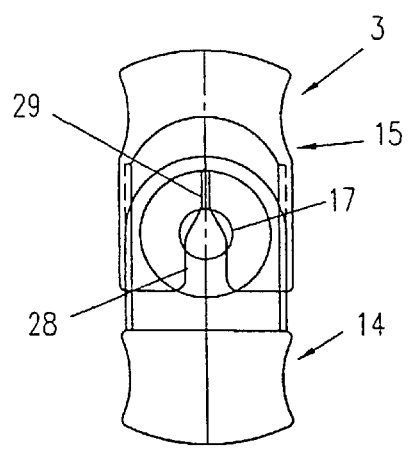
FIG. 4 shows the assembly part of the PEG tube of FIG. 1 as a top view, the retaining clip being in the position in which the assembly part of the PEG tube is freely slidable.

FIG. 3 shows a retaining clip 15 as a top view. The retaining clip 5 is equipped with an essentially rectangular base plate 22 with rounded edges which can be laid by its flat underside 23 onto the abdominal wall 30 of the patient (FIG. 1). Along the two longitudinal sides and one of the front sides of the base plate 22, there is an edge 24 all around. The dimensions of the retaining housing 14 and the retaining clip 15 are such that the retaining parts 16 of the retaining housing 14 can be pushed to fit into the retaining clip 15. In this case, longitudinal grooves 25 in the peripheral edge 24 of the retaining clip 15 and the longitudinal lugs 26 on the retaining part 16 of the retaining housing 14 form a guide. FIGS. 4 and 5 show the parts of the assembly part 3 pushed together as a top view.

In the base plate 22 of the retaining clip 15, there is a longitudinal slit 27 whose diameter decreases in the longitudinal direction. The slit 27 has a first section 28 with a larger diameter that the tube 1 and a second section 29 with a smaller diameter than the tube 1.

The guide of the retaining housing 14 and retaining clip 15 has two stop positions. The retaining clip can be fixed in an engaged manner in the retaining housing e.g. by lugs and corresponding recesses. In the first stop position, the retaining clip is pushed into the retaining housing only so far that the first section 28 of the slit 27 in the retaining clip 15, which section has a larger diameter than the tube, is in alignment with the central bore 17 in the retaining housing 14 such that the assembly part 3 is freely displaceable on the tube (FIG. 4). In the second stop position, the second section 29 of the slit 27 which has a smaller diameter than the tube, is in alignment with the central bore 17 such that the tube is fixed in the assembly part (FIG. 5).

Fitting of the adapter 2 of the PEG tube 1 can take place as follows. To fit the adapter, the tube 1 is first inserted into the bore 17 of the retaining housing 14 and the retaining housing is closed. Subsequently, the retaining clip 15 is pushed on to the retaining housing up to the first stop position (FIG. 4). The assembly part 3 of the adapter is then pushed forward on the tube until the underside 23 of the retaining clip 15 rests flat on the abdominal wall 30. Subsequently, the retaining clip is pushed forward on the retaining housing into the second stop position such that the tube is secured, preventing it from sliding back (FIG. 5). The protruding end of the tube is then cut off directly above the assembly part 3.

However, preferably, the adapter is fitted as follows. In the case of the preferred embodiment, the external retaining part 5 of the adapter 2 is already inserted, in a lightly clamped position, in the cut-out 21 of the retaining housing 14 already inserted into the retaining clip 15, before the assembly, the retaining clip being in the first stop position. The tube is inserted into the bore 17 and the assembly part pushed forward together with the retaining plate of the adapter onto the abdominal wall. Subsequently, the tube is fixed with the assembly part and cut to the required length.

The cylindrical cone 12 of the second clamp part 11 of the adapter 2 is then introduced into the tube 1 and the retaining housing 14 and/or the retaining clip 15 is then pushed back into the first stop position such that the two halves of the retaining housing are still held together but the tube is already freely moveable. Subsequently, the upper clamp part 11 is screwed together with the lower clamp part 8 of the adapter 2, the lower clamp part 8 being held by the external retaining part 5 and the upper clamp part 10 being rotated.

The retaining clip is then pulled off from the retaining housing and the retaining housing is removed after opening of the two housing halves. Since the assembly plate serves as a loose spacer part which creates a distance between the external retaining part 5 of the adapter 2 and the abdominal walls 30 of approximately 5 to 7 mm, mm, the tube 1 has sufficient "play".

Alternatively, the external retaining part 5 of the adapter 2 can be turned together with the lower clamp part 8 and the upper clamp part 11 of the adapter held tight. In this way, turning of the tube in the stoma canal can be avoided.

The assembly part according to the invention permits simple and secure fixing of the PEG adapter. Errors by cutting off the tube at the wrong place leading to the wrong tube length can be avoided. The assembly part facilitates the secure mounting of the external retaining part and the lower clamp part of the adapter thus avoiding pressure being exerted onto the abdominal wall of the patient. If the assembly part forms a unit with the adapter which can be released, handling is further simplified.

The invention claimed is:

1. Clip assembly for use with an adapter to the proximal end of a PEG tube, said clip assembly (3) comprising:
    a retaining housing (14), equipped with a cut-out (21), and a retaining part (16) with a central bore (17) for passing the PEG tube through it; and
    a retaining clip (15),
    wherein the retaining housing (14) is configured for encasing a PEG tube, said PEG tube comprising a distal end and an open proximal end, and further including on its distal end an internal retaining part, supported on a stomach wall of a patient,
    wherein the cut-out (21) is configured for inserting an external retaining part of an adapter to the proximal end of the PEG tube, wherein said adapter is supported on the abdominal wall of the patient, said external retaining part further including elements for connecting the PEG tube and elements for connecting a conduction system to the PEG tube,
    wherein the retaining clip (15) is configured for fixing the PEG tube to prevent it from sliding back, and
    wherein the retaining clip (15) is equipped with a slit (27) for the lateral insertion of the PEG tube, the slit having a first section (28) with a diameter larger than the tube, in which the tube is freely moveable, and a second section (29) with a diameter smaller than the tube, in which the tube is fixed, and
    wherein the retaining housing (14) is equipped with a guide (26) and the retaining clip (15) are equipped with complementary guide portions (26, 25) to facilitate fitting the retaining housing (14) into the retaining clip (15).

2. The clip assembly according to claim 1 wherein the retaining housing (14) is equipped with a gripping part (18).

3. The clip assembly according to claim 2 wherein the gripping part (18) of the retaining housing (14) is equipped with lateral gripping recesses (19).

4. The clip assembly according to claim 2 wherein the retaining part (16) and gripping part (18) of the retaining housing (14) consists of two halves (16', 16"; 18', 18") that can be opened.

5. The clip assembly according to claim 2 wherein the halves (16', 16"; 18', 18") of the retaining part (16) and gripping part (18) are flexibly connected with a hinge (20), in particular a film hinge.

6. The clip assembly according to claim 4 wherein the cut-out (21) is formed for fixing the external retaining part in a clamping position.

7. The clip assembly according to claim 1 wherein the guide (25, 26) has a first and a second stop position, the first section (28) of the slit (27) of the retaining clip (15) being in alignment, in the first stop position, with the bore (17) of the retaining housing (14) and the second section (29) of the slit of the retaining clip being in alignment, in the second stop position, with the bore of the retaining housing.

8. A method of attaching an adapter to the proximal end of a PEG tube, comprising:
    inserting the proximal end of a PEG tube through a central bore of a clip assembly part, said clip assembly part comprising:
        a retaining housing having the central bore for encasing a PEG tube, said retaining housing consisting of two halves flexibly connected by a hinge; and
        a retaining clip, slidably engageable with the retaining housing, said retaining clip including a graduated central slit for fixing the PEG tube;
    slidably engaging the retaining housing with the retaining clip, thereby fixing the PEG tube at a predetermined length;
    attaching an adapter to the proximal end of the PEG tube; and
    slidably disengaging the retaining housing from the retaining clip, thereby
    removing the clip assembly part from the PEG tube, wherein the retaining housing is equipped with a cut-out, configured for inserting an external retaining part of an adapter to the proximal end of a PEG tube.

* * * * *